United States Patent [19]
Don Michael

[11] Patent Number: 5,195,955
[45] Date of Patent: Mar. 23, 1993

[54] DEVICE FOR REMOVAL OF EMBOLIC DEBRIS

[76] Inventor: T. Anthony Don Michael, 309 Panorama Dr., Bakersfield, Calif. 93305

[21] Appl. No.: 492,580

[22] Filed: Mar. 13, 1990

Related U.S. Application Data

[63] Continuation-in-part of Ser. No. 435,887, Nov. 14, 1989, abandoned.

[51] Int. Cl.$^5$ .................. A61B 17/20; A61M 29/00
[52] U.S. Cl. ................................ 604/22; 604/101; 604/102; 606/194
[58] Field of Search ................ 604/96–102, 604/103, 104, 22; 606/7, 194.5

[56] References Cited

U.S. PATENT DOCUMENTS

| | | | |
|---|---|---|---|
| 4,395,806 | 8/1983 | Wonder | 606/195 |
| 4,575,371 | 3/1986 | Nordquist et al. | 604/100 |
| 4,630,609 | 12/1986 | Chin | 604/101 |
| 4,697,573 | 10/1987 | Schiff | 604/264 |
| 4,751,924 | 6/1988 | Hammerschmidt | 604/100 |
| 4,771,777 | 9/1988 | Horzewski | 606/194 |
| 4,790,315 | 12/1988 | Mueller | 604/96 |
| 4,823,812 | 4/1989 | Eschel et al. | 604/96 |
| 4,921,478 | 5/1990 | Solano et al. | 604/96 |
| 4,924,863 | 5/1990 | Sterzer | 606/27 |
| 4,930,496 | 6/1990 | Bosley, Jr. | 604/101 |
| 4,944,745 | 7/1990 | Sogard et al. | 604/96 |
| 4,958,634 | 9/1990 | Jang | 604/103 |
| 4,983,167 | 1/1991 | Sahota | 604/96 |
| 5,059,178 | 10/1991 | Ya | 604/101 |

FOREIGN PATENT DOCUMENTS

| | | | |
|---|---|---|---|
| 0355996 | 2/1990 | European Pat. Off. | |
| 0362146 | 4/1990 | European Pat. Off. | 604/99 |
| 2847633 | 5/1979 | Fed. Rep. of Germany | |

Primary Examiner—Michael H. Thaler
Assistant Examiner—Mark Bockelman
Attorney, Agent, or Firm—Spensley Horn Jubas & Lubitz

[57] ABSTRACT

A device for temporarily blocking a blood vessel of a patient during a procedure for removing an obstruction deposited on the blood vessel wall. The device includes: a catheter having a proximal end and a distal end and arranged to be inserted into the blood vessel via the distal end, the catheter having a peripheral wall and being provided with first and second lumens extending from the proximal end, the first lumen extending fully to the distal end of the catheter, a first opening extending from the first lumen to the peripheral wall for communication with the interior of the blood vessel in order to permit blood flow from a point upstream of the obstruction and through the first lumen to the distal end of the catheter, and a second opening extending from the secon lumen to the peripheral wall at a location between the first opening and the distal end of the catheter; and a balloon secured to the periphral wall and having an inflation opening communicating with the second opening. The balloon is configured such that upon being inflated, it expands eccentrically with respect to the longitudinal axis of the catheter in order to urge the catheter toward the blood vessel wall. The balloon catheter may be used with embolic removal device such as ultrasonic probes and suction catheters.

9 Claims, 2 Drawing Sheets

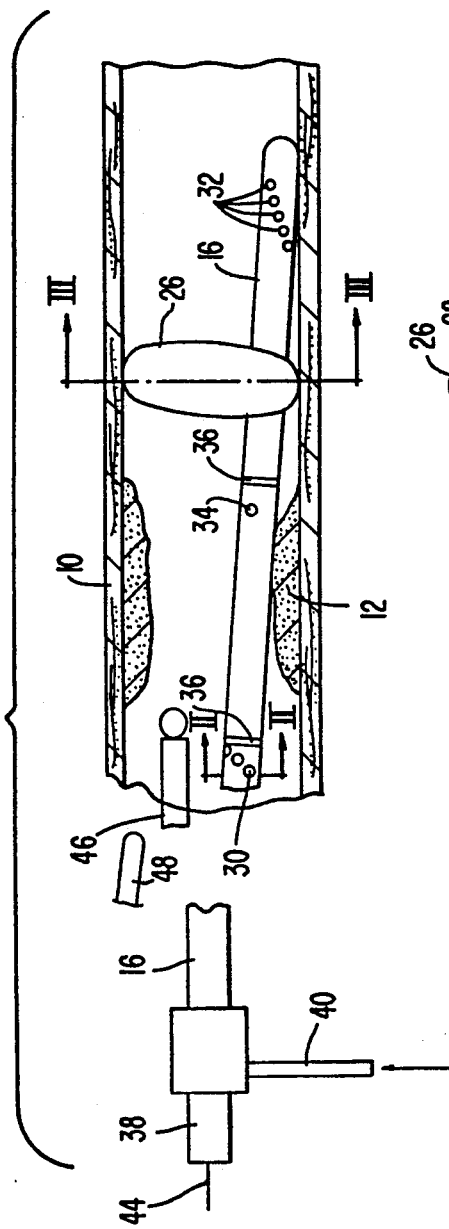

ns in which obstruction removal devices are introduced into a blood vessel at a point which is close to the surface of the skin and are then moved along the blood vessel to the site of an obstruction. Such devices employ lasers, rotoblades, or ultrasound, for example.

DEVICE FOR REMOVAL OF EMBOLIC DEBRIS

CROSS-REFERENCE TO RELATED APPLICATION

This application is a continuation-in-part of U.S. application Ser. No. 435,887, filed on Nov. 14, 1989, and abandoned subsequent to the filing of this application.

BACKGROUND OF THE INVENTION

The present invention relates to the removal of embolic debris from blood vessels, and particularly at locations which cannot be safely reached by surgical techniques.

It is known that severe medical conditions can be caused by the formation, in blood vessels, of plaque or thrombi which frequently narrow the blood flow passage in a vessel to an extent which places an undue burden on the heart or severely limits the ability to supply blood to various organs.

While a number of techniques for dealing with this problem have been proposed, many of these techniques are surgical in nature in that they require direct access to the site of such obstruction. In many cases, this is not medically possible. A significant example is cerebral blood vessels which cannot be safely exposed by surgical techniques.

Recent years have seen the introduction of less invasive techniques in which obstruction removal devices are introduced into a blood vessel at a point which is close to the surface of the skin and are then moved along the blood vessel to the site of an obstruction. Such devices employ lasers, rotoblades, or ultrasound, for example.

The use of such procedures leads to the creation of debris constituted by small particles of the plaque or thrombus and, in the absence of special measures, these particles will be carried along in the blood flow. Particularly in small vessels, such as cerebral vessels, these particles can cause damage to organs downstream of the obstruction.

While suction may be used concurrently with the obstruction removal operation, this will not always effect complete withdrawal before some debris particles or emboli have moved out of the suction region.

Catheters are known in the art which are equipped with blood vessel blocking balloons and which are employed for various purposes, including balloon angioplasty (U.S. Pat. No. 4,581,017) and control of direction of blood flow (U.S. Pat. No. 4,592,340). It appears to be the universal practice to provide balloons which inflate symmetrically around the catheter in order to center the catheter in the blood vessel.

SUMMARY OF THE INVENTION

It is a primary object of the present invention to facilitate the extraction, from the blood stream, of all emboli created during a procedure for clearing an obstruction in the blood vessel.

Another object of the invention is to reliably prevent emboli formed during an obstruction removal procedure from flowing through the blood vessel downstream of the site of the obstruction.

Another object of the invention is to permit a flow of blood to be maintained downstream of the obstruction during a removal procedure.

Still another object of the invention is to provide a device which will prevent the flow of emboli produced during an obstruction removal operation through the blood stream, while facilitating the introduction of separate removal devices, and which can be introduced to the site of the obstruction by a standard percutaneous technique.

The above and other objects are achieved, according to the present invention, by a device for temporarily blocking a region of a blood vessel of a patient during a procedure for removing embolic material deposited on the blood vessel wall, which device allows blood flow through the vessel beyond the blocking region, the device comprising:

a catheter having a proximal end, a distal end and a longitudinal axis intersecting the ends, and arranged to be inserted into the blood vessel via the distal end, the catheter having a peripheral wall and being provided with first and second lumens extending from the proximal end, the first lumen extending fully to the distal end of the catheter, a first opening extending from the first lumen to the peripheral wall for communication with the interior of the blood vessel in order to permit blood flow from a point upstream of the embolic material and through the first lumen to the distal end of the catheter, and a second opening extending from the second lumen to the peripheral wall at a location between the first opening and the distal end of the catheter; and a balloon secured to the peripheral wall, the balloon having an inflation opening communicating with the second opening and being constructed to be inflated into a configuration which is eccentric with respect to the longitudinal axis of the catheter.

The balloon catheter may be used along with embolic material removal devices such as ultrasonic probes and suction catheters.

BRIEF DESCRIPTION OF THE DRAWING

FIG. 1 is a cross-sectional view of a preferred embodiment of a device according to the present invention inserted into a blood vessel.

FIG. 2 is a cross-sectional view taken along the line II—II of FIG. 1 and to a larger scale than FIG. 1.

FIG. 3 is a cross-sectional view taken along the line III—III of FIG. 1.

FIG. 4 is a cross-sectional view in the same plane as that of FIG. 3 but showing the device in a configuration prior to sealing of the blood vessel.

DESCRIPTION OF THE PREFERRED EMBODIMENTS

Figure 5:
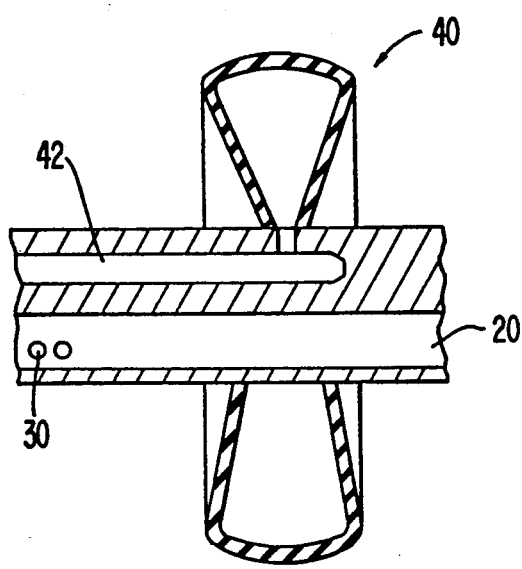
FIG. 5 is a cross-sectional detail view illustrating a further preferred embodiment of the invention.

FIG. 1 shows a preferred embodiment of the device according to the present invention inserted into a blood vessel 10 in which there has developed a partial obstruction 12 which may be constituted by plaque or a thrombus.

Referring to FIGS. 2 and 3 in conjunction with FIG. 1, the device according to the invention is composed essentially of a catheter 16 provided with a first lumen 20 and a second lumen 22. Catheter 16 carries a balloon 26 which is shown in its inflated state in FIGS. 1 and 3 and in its deflated state in FIG. 4. Balloon 26 has an inflation opening 28 which communicates with lumen 22 via a hole extending between lumen 22 and the outer surface of catheter 16. The distal end of lumen 22 is located in the vicinity of opening 28.

Balloon 26 is constructed as a high compliance volume balloon, i.e., relatively low air pressure will act to inflate it to a substantial extent to enable the balloon to obstruct vessel 10 without imposing any substantial radial force which would act to stretch the vessel wall.

Catheter 16 is provided with two or more perfusion holes 30, each of which holes extends between lumen 20 and the outer surface of catheter 16 to communicate with the interior of blood vessel 10. Holes 30 are located between the proximal end of catheter 16 and balloon 26.

Preferably, a plurality of holes 30 are provided and are disposed at various locations around the circumference of catheter 16 along each side of lumen 20. The number and size of holes 30 are selected on the basis of existing space limitations and the desired rate of blood flow through lumen 20.

At the distal end of catheter 16, to the right of balloon 26 in FIG. 1, lumen 20 opens to the interior of blood vessel 10. In addition, the distal end of catheter 16 is provided with a plurality of outlet holes 32 communicating with lumen 20, spaced around the circumference of catheter 16 in the same manner as holes 30.

The proximal end of catheter 16, shown at the left-hand side of FIG. 1, will be located outside of the patient's body and is provided with suitable couplings 38 and 40 having passages which communicate with lumens 20 and 22, respectively.

The purpose of the device thus far described is to prevent particles created during disintegration of obstruction 12 from flowing downstream through blood vessel 10 while permitting a flow of blood, through holes 30 and lumen 20, past obstruction 12 and balloon 26, and then out through holes 32 and the distal end of lumen 20, during such a removal operation.

Catheter 16 may optionally be additionally provided with a third lumen 24 and one or more additional holes 34 extending between lumen 24 and the outer surface of catheter 16 to communicate with the interior of blood vessel 10 and a location just upstream of balloon 26. The distal end of lumen 24 is located in the vicinity of holes 34. Lumen 24 and holes 34 may be employed as a suction path for removing particles from the region upstream of balloon 26. However, as will be described in greater detail below, it is preferred that particle removal be effected by a separate suction catheter which can have a suction lumen larger than lumen 24.

Catheter 16 is additionally provided with radiopaque markers 36, here in the form of bands, located to allow X-ray observation of the position of catheter 16 and balloon 26 relative to obstruction 12.

As shown in FIGS. 1 and 3, balloon 26 is formed to expand eccentrically, or asymmetrically, relative to the axis of catheter 16, i.e., the expansion pattern of balloon 26 is centered on a line extending radially from the axis of catheter 16. As a result, although balloon 26 has sufficient compliance to conform to the interior cross section of vessel 10, it tends, during expansion, to urge catheter 16 away from the axis, or center, of vessel 10. This creates, in vessel 10, a greater clearance for insertion of a further device 46, typically including a catheter, which is operative to break up an obstruction 12, and the simultaneous or subsequent insertion of a separate suction device 48, typically constituted by a catheter having a single relatively large lumen extending fully between its proximal and distal ends.

Preferably, device 46 is an ultrasonic probe of the type described in U.S. Pat. No. 4,870,953, issued to T. Anthony Don Michael, et al., on Oct. 3, 1989. Other known types of obstruction removal devices, such as those utilizing blades or lasers, would be likely to damage catheter 16 and should therefore not be used for the practice of the invention.

The system described above will be used as follows.

First, a thin guidewire 44 is introduced into blood vessel 10 using a standard percutaneous procedure, the guidewire being introduced at a location upstream of blockage 12 and being moved through vessel 10 to a location downstream of blockage 12. Then catheter 16 is placed over guidewire 44 so that guidewire 44 extends through lumen 20, with balloon 26 being deflated, as shown in FIG. 4, and catheter 16 is then advanced through blood vessel 10 until balloon 26 reaches a point downstream of blockage 12.

After catheter 16 has reached the desired location, the existence of flow through the catheter may be checked by injecting contrast medium into lumen 20 and observing the flow of contrast medium by fluoroscopy. Fluid, such as air under pressure, is introduced into lumen 22 via coupling 40 in order to inflate balloon 26 until balloon 26 substantially completely blocks blood vessel 10, as shown in FIG. 1. At this point, a certain level of blood flow continues to occur past balloon 26 via openings 30, lumen 20, which communicates, at the distal end of catheter 16, with the region of blood vessel 10 downstream of balloon 26, and openings 32. Because of the pressure differential upstream and downstream of balloon 26, there will be very little tendency for blood to flow back toward the proximal end of catheter 16. Inflation of balloon 26 moves catheter 16 toward the wall of vessel 10, leaving a region available for insertion of other devices.

Then, the separately introduced removal device 46 is inserted and operated to disintegrate, or break up, obstruction 12, forming particles which are trapped in blood vessel 10 upstream of balloon 26.

Then, a suction catheter (not shown) may be introduced, either in place of or in addition to the catheter associated with removal device 46, upstream of the region of blockage 12, and hyperresuction is performed to remove blood and particles trapped upstream of balloon 26. Alternatively, or in addition, suction can be performed via opening 34 and optional lumen 24.

The sequence of removal and suction can be repeated as often as necessary to reduce obstruction 12 to an acceptable level.

After the procedure has been completed, balloon 26 is allowed to deflate, thereby restoring circulation through blood vessel 10, and catheter 16 is removed.

The procedures described above can be successfully performed with a catheter having a size of approximately 4-8 French. The size of the catheter depends to a considerable degree on the size of blood vessel 10 and the initial size of obstruction 12.

Obturation of openings 30, 32 and 34 is prevented by arranging several such openings at spaced locations about the circumference of catheter 16.

According to one preferred embodiment of the invention for removing obstructions from larger blood vessels, catheter 16 can be a large angioplasty catheter equipped, as shown in FIG. 5, with a further balloon, or cuff, 40 which is shown in its inflated state and is inflated with air under pressure supplied via an additional lumen 42.

Balloon 40 is a low compliance pressure balloon whose inflation requires an air pressure higher than that required by balloon 26. When balloon 40 is inflated, it produces a substantial outward radial force which has the effect of breaking up obstruction 12, after which balloon 40 is deflated and the resulting plaque particles can be suctioned out in the manner described earlier herein.

Balloon 40 is constructed to encircle catheter 16 upon being inflated and will be mounted between markers 36 of the structure shown in FIG. 1.

According to a further feature of the present invention, the balloon carried by catheter 16 for obstructing a blood vessel is configured such that, upon inflation, the outer wall surface of the balloon at the side facing in the upstream direction of blood flow will take on a concave curvature. This will cause the balloon to form a pocket which more efficiently traps debris particles until they are subsequently removed by suction.

Figure 8:
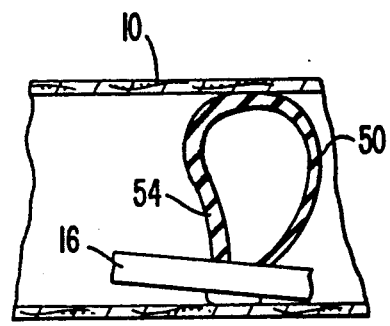
FIG. 8 is a detail view showing the component of FIG. 6 in its active condition.
Figure 6:
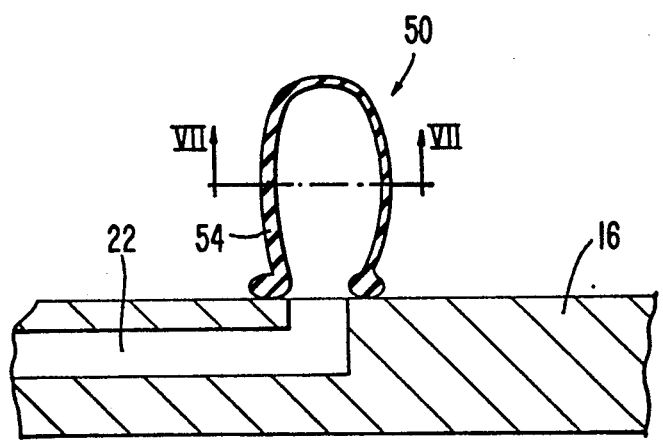
FIG. 6 is a cross-sectional detail view of a component provided in another embodiment of the invention.
Figure 7:
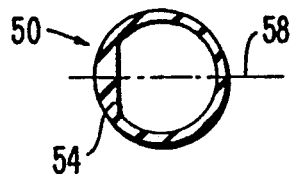
FIG. 7 is a cross-sectional view along line VII—VII of FIG. 6.

FIGS. 6–8 show a balloon 50 constituting such an embodiment of the invention, FIGS. 6 and 7 showing balloon 50 in its deflated state and FIG. 8 showing balloon 50 in its inflated state.

As shown in FIGS. 6 and 7, balloon 50 is provided at its upstream side with a thickened wall portion 54 the thickness of which decreases progressively from the region of the balloon inflation opening to the region remote from the inflation opening. In addition, the thickness of wall portion 54 decreases progressively in directions at right angles to a plane containing the axis of catheter 16 and a center line 58 which extends parallel to the axis of catheter 16.

The manner of manufacturing a balloon to have a wall thickness which varies in this manner is known in the balloon fabrication art.

Balloon 50 is preferably a high compliance volume balloon and as a result of the configuration of the wall of balloon 50, the balloon will expand to fill the internal cross section of vessel 10 while, because the thickness of wall portion 54 decreases progressively from the balloon inflation opening to the region remote from the inflation opening, the upstream side of balloon 50, the left-hand side in FIGS. 6–8, will expand to a varying degree in the upstream direction. Specifically, the expansion in that direction will increase progressively from the inflation opening to the region remote from the inflation opening. As a result, the outer wall surface of the upstream side of balloon 50 will assume a concave form, as shown in FIG. 8, at least in the region adjacent catheter 16.

In FIG. 8, balloon 50 is fully expanded so that the outer periphery of the expanded balloon contacts blood vessel wall 10 to block blood flow in the annular region between catheter 16 and the blood vessel wall.

Conceivably, instead of forming balloon 50 to have a wall thickness which varies locally, the composition of the balloon could be locally varied to produce the desired differential expansion characteristics.

For cases where a blocking catheter must be inserted in the direction counter to blood flow, the position of balloon 50 may be reversed so that the concave outer wall surface faces the distal end of catheter 16.

In many situations, it will be necessary to monitor the rate of blood flow downstream of balloon 26 and the distal end of catheter 16 in order to assure, for example in the case of a carotid artery, that a sufficient flow of blood is being delivered to the patient's brain. For this purpose, use may be made of a Doppler flow meter having a transducer wire placed within blood vessel 10 at a location downstream of the distal end of catheter 16. The transducer wire could be constituted by guidewire 44, inserted to extend beyond the distal end of catheter 16. Alternatively, a separate transducer wire could be secured to the outer surface of catheter 16 or could be embedded within catheter 16, in each case the wire being arranged to extend beyond the distal end of catheter 16. According to another possibility, the transducer wire of the Doppler flow meter could be structurally independent of catheter 16 and could be inserted through the wall of blood vessel 10 at a location downstream of the distal end of catheter 16.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A device for temporarily obstructing a region of a blood vessel of a patient, without imposing any substantial radial force which act to stretch the vessel wall on the blood vessel, during a procedure for removing embolic material deposited on the blood vessel wall, which device allows blood flow through the vessel beyond the region blocked by the device, said device comprising:

a catheter having a proximal end, a distal end and a longitudinal axis intersecting the ends, said catheter being arranged to be inserted into the blood vessel via said distal end, said catheter having a peripheral wall and being provided with first and second lumens extending from said proximal end, said first lumen extending fully to said distal end of said catheter, a first opening extending from said first lumen to said peripheral wall for communication with the interior of the blood vessel in order to permit blood flow from a point upstream of the embolic material and through said first lumen to said distal end of said catheter, and a second opening extending from said second lumen to one side of said peripheral wall at a location between said first opneing and said distal end of said catheter; and a high compliance volume balloon secured to said peripheral wall, said balloon having an inflation opening surrounding said second opening and located at the one side of said peripheral wall, the compliance of said balloon being such that when said catheter is inserted into the blood vessel and said balloon is being inflated, sid balloon expands eccentrically around and excircling a major portion of said catheter and expands radially to conform substantially to the interior cross section of the blood vessel, without stretching the blood vessel wall, in order to substantially completely block the blood vessel while urging said catheter away from the center of the blood vessel.

2. A device as defined in claim 1 further comprising coupling means connected to said proximal end of said catheter for establishing communication between said lumens and a region outside the patient's body when said distal end of said catheter is located witin the blood vessel.

3. A device as defined in claim 2 wherein said coupling means include a passage for introducing air into said second lumen for inflating said balloon.

4. A device as defined in claim 2 wherein said catheter is provided with a plurality of first openings.

5. A device as defined in claim 2 wherein the sapcing between said first opening and said balloon, along the longitudinal axis of said catheter, is greater than the length of the embolic maerial deposit to be removed.

6. A device for temporarily blocking a region of a blood vessel of a patient, without imposing any substantial radial force on the blood vessel, during a procedure for removing embolic material deposited on the blood vessel wall, which device allows blood flow through th vessel beyond the region blocked by the device, said device comprising:
 a catheter having a proximal end, a distal end and a longitudinal axis intersecting the ends, said catheter being arranged to be inserted into the blood vessel via said distal end, said catheter having a peripheral wall and being provided with first and second lumens extending from said proximal end, said first lumen extending fully to said distal end of said catheter, a first opening extending from said first lumen to said peripheral wall for communication with the interior of the blood vessel in order to permit blood flow from a point upstream of the embolic material and through said first lumen to said distal end of said catheter, and a second opening extending from said second lumen to said peripheral wall at a location between said first opening and said distal end of said catheter; and
 a high compliance volume balloon secured to said peripheral wall, said balloon having an inflation opening communicating with said second opening, said balloon being inflatable into a configuration which is eccentric with respect to the longitudinal axis of said catheter and which substantially completely surrounds said catheter wherein said balloon is constructed to have wall portions with respectively different expansion characteristics such that, upon inflation of said balloon the exterior surface of a side of said balloon which faces one end of said catheter has a concave portion with a tangent surface that is substantially normal to said catheter longitudinal axis.

7. A device as defined in claim 6 wherein said balloon has a wall portion which decreases in thickness in a direction away from said inflation opening.

8. A device for temporarily obstructing a region of a blood vessel of a patient, without imposing any substantial radial force which act to stretch the vessel wall on the blood vessel, during a procedure for removing embolic material deposited on the blood vessel wall, which device allows blood flow through the vessel beyond the region blocked by the device, said device comprising:
 a catheter having a proximal end, a distal end and a longitudinal axis intersecting the ends, said catheter being arranged to be inserted into the blood vessel via said distal end, said catheter having a peripheral wall and being provided with first and second lumens extending from said proximal end, said first lumen extending fully to said distal end of said catheter, a first opening extending from said first lumen to said peripheral wall for communication with the interior of the blood vessel in order to permit blood flow from a point upstream of the embolic material and through said first lumen to said distal end of said catheter, and a second opening extending from said second lumen to said peripheral wall at a location between said first opening and said distal end of said catheter; and
 a high compliance volume balloon secured to one side of said peripheral wall, said balloon having an inflation opening surrounding said second opening, the compliance of said balloon being such that when said catheter is inserted into the blood vessel and said balloon is being inflated, said balloon expands eccentrically around and encircling a major portion of said catheter and expands radially to conform substantially to the interior cross section of the blood vessel, without stretching the blood vessel wall, in order to substantially completely block the blood vessel while urging said catheter away from the center of the blood vessel,
 in combination with an ultrasonic probe for disintegrating embolic material, said probe being structurally independent of, and movable relative to, said catheter and being insertable into the blood vessel adjacent said catheter to a location which is spaced from said balloon along the longitudinal axis of said catheter.

9. A combination as defined in claim 11 further comprising a suction catheter insertable into the blood vessel separately from, and adjacent, said first-recited catheter for removing embolic debris after disintegration of embolic material by said probe.

* * * * *